United States Patent [19]

Nedwick

[11] Patent Number: 5,043,481
[45] Date of Patent: Aug. 27, 1991

[54] CYCLOHEXANE OXIDATION

[75] Inventor: Robert Nedwick, Broomall, Pa.

[73] Assignee: Arco Chemical Technology, Inc., Wilmington, Del.

[21] Appl. No.: 590,620

[22] Filed: Sep. 28, 1990

[51] Int. Cl.[5] .................... C07C 409/14; C07C 407/00
[52] U.S. Cl. ..................................... 568/570; 568/569
[58] Field of Search ....................... 568/570, 561, 569

[56] References Cited

U.S. PATENT DOCUMENTS 2,825,742  3/1958  Schueler et al. .................... 568/570
4,055,600  10/1977  Langley et al. ..................... 568/570

FOREIGN PATENT DOCUMENTS 2552119  5/1976  Fed. Rep. of Germany ...... 568/570

Primary Examiner—Werren B. Lone
Attorney, Agent, or Firm—William C. Long

[57] ABSTRACT

The present invention relates to the oxidation of a cycloalkane to produce a product comprised of cycloalkylhydroperoxide with the removal of a vapor stream from the oxidation zone wherein oxidation products such as hydroperoxide, cycloalkanol and cycloalkanone are separated from the removed stream before the stream is recycled to the oxidation zone.

4 Claims, 1 Drawing Sheet

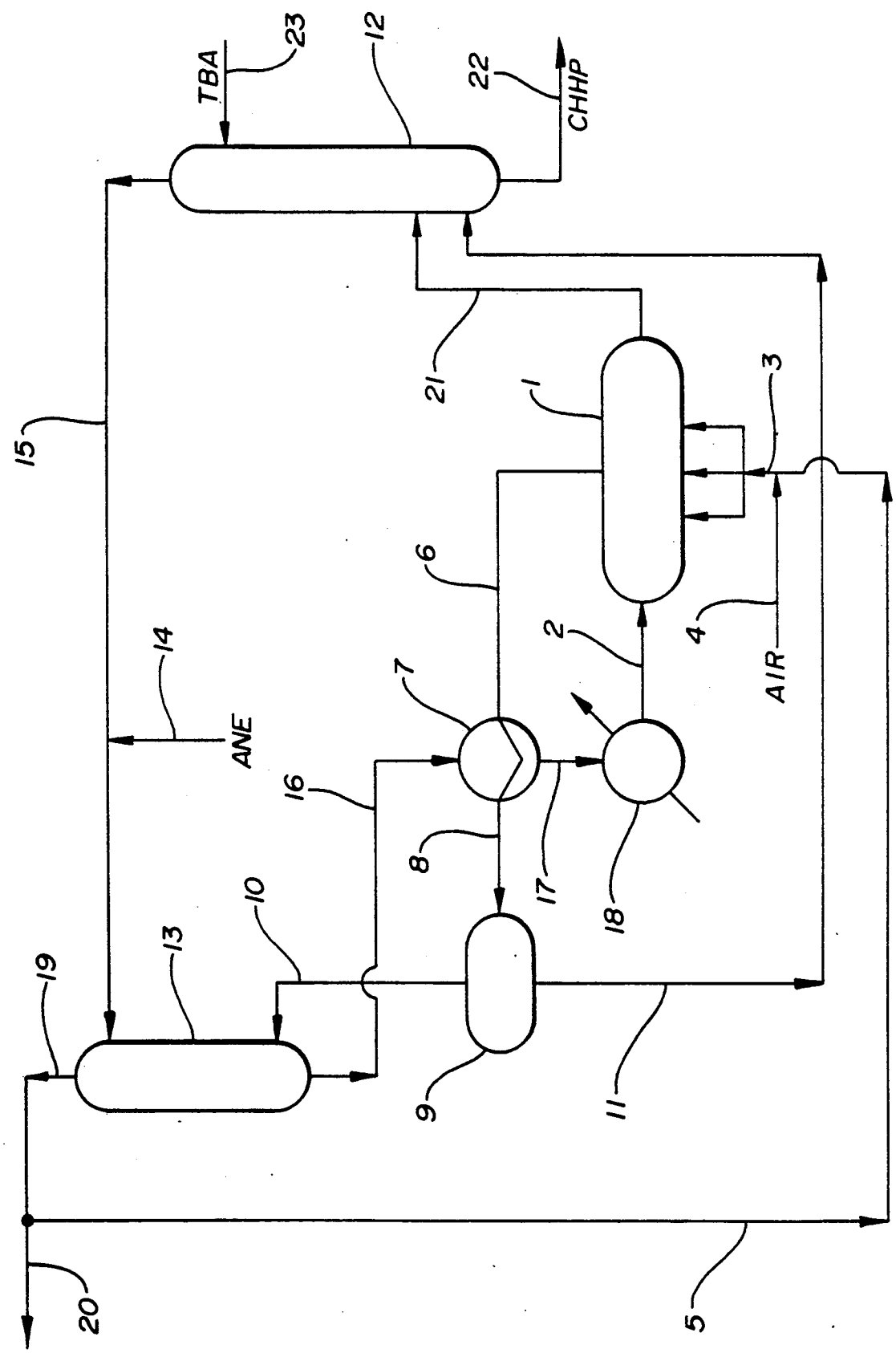

CYCLOHEXANE OXIDATION

BACKGROUND OF THE INVENTION

1. Field of the Invention

The present invention relates to the molecular oxygen oxidation of a cycloalkane such as cyclohexane to produce a product mixture comprised of cycloalkylhydroperoxide wherein during the oxidation a vapor stream is removed from the oxidation zone, condensed and returned to the oxidation zone, the improvement being separation of cycloalkane oxidation products such as the hydroperoxide, cycloalkanol and cycloalkanone from the said stream before the stream is returned to the oxidation zone.

2. Description of the Prior Art

The oxidation of cyclohexane to form products including cyclohexylhydroperoxide (CHHP) is a known reaction.

U.S Pat. 3,927,115 shows the oxidation of cyclohexane with molecular oxygen to form CHHP, cyclohexane and cyclohexanone, the improvement being carrying out the oxidation in the presence of an alkane having a tertiary carbon, eg. isobutane.

U.S. Pat. Nos. 3,949,003 and 3,987,115 show the oxidation of cyclohexane in the presence of a tertiary alcohol and a tertiary hydroperoxide to produce CHHP, cyclohexanol and cyclohexanone.

U.S Pat. No. 3,949,004 shows oxidation of cyclohexane in the presence of a stabilizing agent such as water or tertiary butyl alcohol to produce CHHP, cyclohexanol and cyclohexanone.

U.S. Pat. No. 4,080,387 relates to oxidation of cyclohexane to a product mixture comprised of CHHP, cyclohexanol and cyclohexanone and to the concentration of CHHP by distillation procedures.

U.S. Pat. No. 2,675,407 describes the oxidation of a cycloalkane dissolved in tertiary butyl alcohol.

U.S. Pat. No. 2,851,496 describes the oxidation of cyclohexane including reacting the product mixture in the presence of a peroxide decomposition catalyst to reduce the CHHP content.

U.S. Pat. 3,365,490 relates to the production of adipic acid by oxidizing cyclohexane, separating the reaction mixture with recycle of unreacted cyclohexane and subsequent nitric acid oxidation of the cyclohexanol and cyclohexanone to form adipic acid.

U.S. Pat. No. 3,365,490 relates to the oxidation of cycloalkanes to hydroperoxides and includes a basic treatment of recycle cycloalkane.

U.S. Pat. No. 3,694,511 describes the hydrogenation of cycloalkane by peroxides under conditions effective to preserve catalyst life and activity.

U.S Pat. No. 3,719,706 separates by-products form cyclohexyl hydroperoxide by water washing.

U.S. Pat. No. 3,923,895 treats the hydroperoxide containing solution in cycloalkane by heating in the presence of a chromium catalyst in order to obtain cyclohexanone and cyclohexanol.

U.S. Pat. No. 3,927,108 is also concerned with the hydrogenation of cyclohexylhydroperoxide in the presence of a particular catalyst.

U.S. Pat. No. 3,957,876 describes preparation of CHHP by oxidation of cyclohexane containing a cobalt catalyst in a specially zoned oxidation reactor.

U.S. Pat. No. 4,326,084 shows oxidation of cyclohexane to produce a mixture containing CHHP and decomposing this latter material with a particular, designated catalyst.

U.S. Pat. No. 4,341,907 describes oxidation of cyclohexane in the presence of a particular heavy metal compound catalyst.

U.S. Pat. No. 4,465,861 describes decomposition of a reaction mixture containing a CHHP using a specified catalyst combination.

U.S. Pat. No. 4,482,746 likewise shows decomposition of CHHP using a special catalyst combination of components.

U.S. Pat. No. 4,499,305 similarly describes decomposition of CHHP using a special catalyst.

U.S. Pat. No. 4,503,257 decomposes CHHP by using a catalyst consisting of a certain metal on a solid support.

U.S. Pat. No. 4,720,592 describes extracting a cyclohexane oxidation mixture with water followed by hydrogenation to convert the CHHP.

U.S. Pat. No. 3,917,708 describes the oxidation of cyclohexane using a heavy metal salt catalyst.

U.S. Pat. No. 4,163,027 describes a process for working up cyclohexane oxidation mixture by treatment with alkaline metal compound containing solutions.

U.S. Pat. No. 4,543,427 shows decomposition of CHHP with a supported cobalt catalyst.

U.S. Pat. No. 4,704,476 describes working up a cyclohexane oxidation mixture with aqueous alkali solution.

U.S. Pat. No. 4,814,511 shows working up cyclohexane oxidation mixtures by reaction with cyclo-olefins in the presence of certain, designated catalysts with ultimate hydrogenation of the resulting oxide to the cycloalkanol.

CHHP has been suggested as a reactant for the catalytic epoxidation of olefinically unsaturated compounds such as propylene to form the corresponding oxirane compound. See for example, U.S. Pat. Nos. 3,983,143 and 3,870,729 as well as European Patent 0 129 814.

Generally, a mixture of oxygen and inert gas is employed as the oxidant feed to the oxidation. Air is especially preferred. Vapors are removed from the oxidation reaction zone in order to prevent inerts build-up and/or to remove the oxidation heat of reaction by vaporization of components of the liquid oxidation reaction mixture. In prior practices, the removed vapor is cooled by indirect heat exchange or by direct contact with cool liquid feed to the oxidation zone to condense the readily condensible components including cycloalkane, cycloalkylhydroperoxide, cycloalkanol and cycloalkanone, which are recycled to the oxidation reaction zone. See, for example, U.S. Pat. No. 3,109,864.

However, it has now been found that recycle of the oxidation products, removed as vapor, to the oxidation reaction zone after condensation results in a substantial decrease in oxidation reaction selectivity, especially to the cycloalkylhydroperoxide product.

BRIEF DESCRIPTION OF THE INVENTION

In accordance with the present invention, a cycloalkane such as cyclohexane is oxidized in the liquid phase by contact with a molecular oxygen-containing gas. During the oxidation, a vapor stream which is comprised of unreacted cycloalkane together with significant amounts of cycloalkane oxidation products such as the cycloalkylhydroperoxide, cycloalkanol and the cycloalkanone is removed from the oxidation reaction zone. According to the invention, the withdrawn vapor stream is partially condensed in order to form a liquid condensate phase which contains a predominant amount of the above-mentioned cycloalkane oxidation products. The condensate phase is separated from uncondensed vapors, which latter materials are further cooled to condense unreacted cycloalkane for recycle to the oxidation zone.

DESCRIPTION OF THE DRAWINGS

The attached drawing illustrates schematically practice of the invention.

DETAILED DESCRIPTION OF THE INVENTION

In accordance with the present invention, cycloalkane is oxidized by contact with a molecular oxygen-containing gas at reaction conditions to form oxidation products including the cycloalkylhydroperoxide, cycloalkanol and cycloalkanone. The oxidation conditions are generally well known as evidenced by the prior art recited above. Temperatures ranging from about 80° to 200° C. are usually employed, and reaction pressures are sufficient to maintain cycloalkane in the liquid phase. Preferred temperatures are 130° to 170° C., and especially preferred temperatures are 145° to 155° C. Pressures from atmospheric to 350 psi or higher can be employed, pressures of 100 to 300 psi being preferred.

Various stabilizers and other additives used in the prior art to enhance hydroperoxide formation can be employed.

The molecular oxygen oxidant gas can comprise pure oxygen, but is preferably oxygen admixed with one or more inert gases. Air is especially preferred.

In a particularly preferred practice, the cycloalkane oxidation is carried out in the presence of a stabilizing agent, especially t-butyl alcohol, as described in U.S. Pat. No. 3,949,004, the disclosure of which is incorporated herein by reference.

Referring to the drawing, Zone 1 is the oxidation reaction zone wherein the cycloalkane oxidation takes place. Zone 1 may be a multi-compartmental reactor such as is described in U.S. Pat. No. 4,066,706. Cycloalkane feed, which has been preheated to essentially reaction temperature, is introduced into Zone 1 via Line 2. The molecular oxygen-containing oxidant gas is introduced into Zone 1, preferably at a plurality of entry points, via Line 3. The oxidant stream comprises both net feed introduced via Line 4 as well as recycle vapor which is recycled via Line 5.

Zone 1 is maintained at appropriate conditions of temperature and pressure so as to maintain a reasonable oxidation reaction rate and to maintain the cycloalkane reaction mixture in the liquid phase. Essential to practice of the present invention is the continuous withdrawal of a vapor stream from Zone 1 via Line 6. Removal of this stream is essential since inert gases are generally introduced into the reaction zone with the molecular oxygen oxidant and must be removed in order to prevent pressure build-up. In addition, in an especially preferred mode of operation, the exothermic reaction heat is removed from reaction Zone 1 by means of vaporization of liquid and the removal therefrom as vapor, thus resulting in the removal of the heat of oxidation.

The vapor stream exiting Zone 1 contains, in addition to unreacted oxygen, inert gases and unreacted cycloalkane, small but finite amounts of the desired oxidation products, notably cycloalkylhydroperoxide, cycloalkanol and cycloalkanone. Normally, the vapor mixture is passed to an economizer wherein the vapors are directly contacted with cycloalkane which is to be fed to the oxidation zone whereby the cycloalkane and associated oxidation products are condensed and ultimately returned to the oxidation zone. However, it has been found that such operation results in serious degradation of the oxidation products returned to oxidation Zone 1, thus resulting in an overall inefficiency and loss of selectivity for the process.

In accordance with the present invention, as depicted in the attached drawing, the vapor mixture exiting Zone 1 via Line 6 is passed to cooling Zone 7 wherein the mixture is cooled to a temperature sufficient to condense the predominant portion of the oxidation products contained therein. The cooled mixture passes via Line 8 to vapor/liquid separation Zone 9 wherein the mixture is resolved into a vapor phase exiting via Line 10 and a liquid phase which exits via Line 11. The liquid phase in Line 11 contains more than 50% of the cycloalkylhydroperoxide, cycloalkane and cycloalkanone which was withdrawn from Zone 1 via Line 6. As shown in the drawing, the liquid condensate passes via Line 11 to distillation Zone 12 where, with other process streams, it is concentrated by distillation.

The vapor mixture from separation Zone 9 passes via Line 10 to Economizer 13 wherein these vapors are contacted with liquid cycloalkane. Net cycloalkane is added via Line 14, preferably in combination with a recycle t-butyl alcohol cycloalkane azeotrope passing from Zone 12 via Line 15. In Economizer 13 cycloalkane from Line 10 is condensed, and the liquid cycloalkane and t-butyl alcohol azeotrope are preheated. These materials pass from Zone 13 via Line 16 and are heated in Zone 7 by indirect heat exchange with vapors from reaction Zone 1. The heated materials pass via Line 17 to Heater 18 wherein they are further heated as by indirect exchange with steam and are then passed via Line 2 as feed to oxidation Zone 1.

The vapor stream from Economizer 13 is removed via Line 19 with a portion of the vapor being recycled via Line 5 to Zone 1 and a small portion being purged via Line 20.

The liquid oxidation product containing reaction mixture exits oxidation Zone 1 via Line 21 and passes to distillation Zone 12. In Zone 12, the oxidation product stream from oxidation Zone 1 as well as the condensate from the vapor stream removed from Zone 1 via Line 6 are distilled according to conventional procedures. A product cycloalkylhydroperoxide stream concentrated to the desired degree in the hydroperoxide is removed via Line 22 and may be used, for example, in an associated reaction whereby the hydroperoxide is reacted with propylene to form propylene oxide in accordance with known procedures.

Net t-butyl alcohol make-up is conveniently introduced into distillation Zone 12 via Line 23.

Through practice of the present invention, important improvements in the oxidation selectivity of cycloalkane to the desired oxidation products, most notably the cycloalkylhydroperoxide, is achieved. When compared with prior procedures whereby the entire vapor effluent from the oxidation zone was cooled to condense the condensible components, all of which were returned to the oxidation zone, substantial improvements in efficiency are achieved through practice of the invention. It has been found that the return of oxidation products as condensate to the oxidation zone results in significant degradation and formation of acidic materials. In accordance with the present invention, the separation of these materials from the vapor stream as condensate, which condensate passes to a separation step rather than back to the oxidation step, results in very real and important process benefits which are not suggested by prior workers.

Cyclohexane is the preferred cycloalkane which is oxidized in accordance with the invention. Generally, however, the invention is applicable to cycloalkanes having 5 to 12 carbon atoms such as cyclopentane, cyclo-octane and cyclododecane.

The following example illustrates a particular practice of the invention as it applies to cyclohexane oxidation.

EXAMPLE

Referring to the attached drawing, cyclohexane is oxidized in the liquid phase by reaction with molecular oxygen in accordance with known procedures in oxidation Zone 1. The oxidation temperature is 149° C., and the oxidation zone pressure is maintained at 290 psig. Liquid cyclohexane feed is introduced into Zone 1 via Line 2; net air is introduced by means of Line 4 and 3 in combination with recycle vapors which are introduced into Zone 1 via Lines 5 and 3. Conditions in Zone 1 are controlled in order to provide for maximum selectivity to cyclohexylhydroperoxide, and substantial quantities of cyclohexanol and cyclohexanone are also formed. Conversion of cyclohexane is about 7.5%. A liquid reaction mixture mainly comprised of unreacted cyclohexane together with product cyclohexylhydroperoxide, cyclohexanol and cyclohexanone, is removed from Zone 1 via Line 21 and passed to distillation column 12 for concentration of the oxidation products.

Essential to practice of the invention is the continuous removal from Zone 1 of a vapor mixture via Line 6 which mixture is comprised of unreacted oxygen, nitrogen, unreacted cyclohexane and the oxidation products comprising cyclohexylhydroperoxide, cyclohexanol and cyclohexanone. The vapor mixture passes via Line 6 to Heat Exchanger 7 wherein the mixture of vapors is cooled by indirect heat exchange with cyclohexane feed to a temperature sufficient to condense the predominant amount of cyclohexylhydroperoxide, cyclohexanol and cyclohexanone contained in the mixture of gases. An appropriate temperature is about 135° C. at which about 80% of the cyclohexylhydroperoxide, cyclohexanol and cyclohexanone are condensed. Obviously, this temperature can vary depending both on the pressure of the system and on the percentage of condensation of the oxidation products which is desired. Generally, temperatures in the range of 115°-140° C. are useful at the normal system pressures.

Preheated cyclohexane from Exchanger 7 passe via Line 17 to Heater 18 wherein this stream is heated essentially to the reaction temperature and then passed via Line 2 to the oxidation reaction Zone 1.

The cooled mixture from Exchanger 7 passes via Line 8 to liquid/vapor Separator 9 wherein the mixture is separated into liquid and vapor streams. The liquid stream containing the predominant amount of cyclohexylhydroperoxide, cyclohexanol and cyclohexanone passes via Line 11 to Separation Zone 12 wherein, as above indicated, a stream concentrated in these oxidation products is obtained.

Uncondensed vapor from Zone 9 passes via Line 10 to Economizer 13 wherein the vapors are directly contacted with liquid cyclohexane in order to preheat the cyclohexane and cool the said vapors. Cyclohexane and the oxidation products are condensed in Economizer 13 and are ultimately returned to oxidation Zone 1 via Lines 16, 17 and 2.

A cyclohexane stream from separation Zone 12 passes via Line 15 to Economizer 13 for preheating. Net cyclohexane is introduced via Line 14.

Overhead vapors from Economizer 13 are removed via Line 19; a portion is purged via Line 20 with the predominant portion recycled to oxidation Zone 1 via Lines 5 and 3.

In the embodiment of the invention described in this example, the oxidation is carried out in the presence of a stabilizing amount of tertiary butyl alcohol in accordance with known procedures. The net t-butyl alcohol is introduced into Zone 12 via Line 23 and passes to oxidation Zone 1 along with feed cyclohexane by means of Lines 15, 16, 17 and 2.

Removed from distillation Zone 12 via Line 22 is a stream concentrated in cyclohexylhydroperoxide, cyclohexanone and cyclohexanol. This stream can be used directly in the epoxidation of olefins such as propylene to form the corresponding oxirane compound and a valuable coproduct cyclohexanol/cyclohexanone stream.

An outstanding advantage of practice of the invention is the improved selectivities which are achieved as a result of bypassing the cyclohexane oxidation products removed from oxidation Zone 1 in the vapor stream. Contrasted with conventional procedures which involve returning these components to oxidation Zone 1 after condensation, overall net selectivities on a molar basis to cyclohexylhydroperoxide, cyclohexanone and cyclohexanol can be improved as much as 1.0-1.5%. In a plant of industrial size, savings can be in the millions of dollars per year in improved yields of cyclohexanol and cyclohexanone and in improved yields of propylene oxide where the cyclohexylhydroperoxide is used to epoxidize propylene.

The following table shows the composition in mol.% and quantities of the streams at various points in the example above described:

TABLE 1

| STREAM COMP, MOL % | STREAM NO. | | | | | | |
|---|---|---|---|---|---|---|---|
| | 2,16,17 | 23 | 4 | 5 | 6,8 | 10 | 11 |
| $N_2$ | 1.72 | — | 79.00 | 96.66 | 52.10 | 59.20 | 1.27 |
| $O_2$ | 0.06 | — | 21.00 | 2.81 | 1.53 | 1.73 | 0.04 |
| Cyclohexane | 63.48 | — | — | 0.42 | 24.76 | 20.08 | 58.31 |
| T. B. A. | 34.64 | 100.00 | — | 0.11 | 21.33 | 18.97 | 39.19 |
| Cyclohexanone | 0.02 | — | — | — | 0.05 | 0.01 | 0.25 |
| Cyclohexanol | 0.01 | — | — | — | 0.06 | 0.01 | 0.40 |
| CHHP | — | — | — | — | 0.05 | — | 0.29 |
| Acid & Esters | 0.07 | — | — | — | 0.12 | — | 0.25 |
| TOTAL | 100.00 | 100.00 | 100.00 | 100.00 | 100.00 | 100.00 | 100.00 |
| LBS./HR. | 1,392,400 | 100,000 | 125,000 | 95,000 | 678,880 | 551,410 | 127,470 |

TABLE 1-continued

| STREAM COMP. MOL % | STREAM NO. | | | | | | |
|---|---|---|---|---|---|---|---|
| | 14 | 15 | 20 | 22 | 21 | 3 | 19 |
| $N_2$ | — | 1.28 | 96.66 | — | 1.28 | 86.70 | 96.66 |
| $O_2$ | — | 0.04 | 2.81 | — | 0.04 | 13.08 | 2.81 |
| Cyclohexane | 100.00 | 68.42 | 0.42 | 0.04 | 62.31 | 0.18 | 0.42 |
| T. B. A. | — | 30.25 | 0.11 | 61.12 | 28.94 | 0.04 | 0.11 |
| Cyclohexanone | — | 0.01 | — | 2.76 | 0.52 | — | — |
| Cyclohexanol | — | — | — | 4.88 | 0.90 | — | — |
| CHHP | — | — | — | 23.07 | 4.46 | — | — |
| Acid & Esters | — | — | — | 8.13 | 1.55 | — | — |
| TOTAL | 100.00 | 100.00 | 100.00 | 100.00 | 100.00 | 100.00 | 100.00 |
| LBS./HR. | 71,500 | 1,036,400 | 100,410 | 196,090 | 933,520 | 220,000 | 195,410 |

What is claimed is:

1. The process for the oxidation of a cycloalkane having 5 to 12 carbon atoms in the liquid phase with molecular oxygen to form a product mixture comprising cycloalkylhydroperoxide which comprises:

(a) contacting the said cycloalkane in the liquid phase with molecular oxygen in a reaction zone at conditions effective to form cycloalkylhydroperoxide including temperature in the range of 80° to 200° C. and pressure sufficient to maintain said cycloalkane in the liquid phase;

(b) withdrawing from the said reaction zone a vapor mixture comprises of said cycloalkane and cycloalkane oxidation products including cycloalkylhydroperoxide;

(c) withdrawing from the said reaction zone a liquid stream comprised of said cycloalkane and oxidation products including cycloalkylhydroperoxide;

(d) cooling the said vapor mixture withdrawn from the reaction zone and condensing a predominance of the cycloalkane oxidation products contained therein;

(e) separating the cooled mixture into a liquid cycloalkane oxidation product stream and a vapor stream comprised of said cycloalkane;

(f) condensing said cycloalkane from the cycloalkane vapor stream and recycling the condensed cycloalkane to said reaction zone.

2. The process of claim 1 wherein the cycloalkane is cyclohexane.

3. The process of claim 1 wherein the temperature in step (a) is in the range of 130° to 170° C.

4. The process of claim 1 wherein the temperature in step (a) is in the range of 145° to 155° C.

* * * * *